United States Patent [19]

Boussignac et al.

[11] Patent Number: 5,454,833
[45] Date of Patent: Oct. 3, 1995

[54] SYSTEM FOR TEMPORARILY OBTURATING AN ORIFICE IN A PERFORATED ORGAN, SUCH AS A VESSEL

[75] Inventors: Georges Boussignac, Antony; Pierre Hilaire; Pascal Pendaries, both of Paris, all of France

[73] Assignee: Laboratoire, Nycomed S.A., Paris, France

[21] Appl. No.: 108,905

[22] Filed: Aug. 18, 1993

[30] Foreign Application Priority Data

Jul. 21, 1993 [FR] France .................................. 93 08950

[51] Int. Cl.$^6$ .................................................. A61B 17/04
[52] U.S. Cl. .......................... 606/213; 606/215; 606/230
[58] Field of Search .............................. 606/228, 215, 606/223, 230, 213, 156, 228, 229

[56] References Cited

U.S. PATENT DOCUMENTS

| | | | |
|---|---|---|---|
| 4,587,969 | 5/1986 | Gillis | 606/156 |
| 4,744,364 | 5/1988 | Kensey | 606/213 |
| 5,053,046 | 10/1991 | Janese | 606/215 |
| 5,053,047 | 10/1991 | Yoon | 606/223 |
| 5,108,420 | 4/1992 | Marks | 606/213 |
| 5,123,914 | 6/1992 | Cope | 606/215 |
| 5,292,332 | 3/1994 | Lee | 606/215 |

Primary Examiner—Gary Jackson
Attorney, Agent, or Firm—Ladas & Parry

[57] ABSTRACT

A system for obturating an orifice in a perforated organ or vessel such as a vessel having undergone an operation. In the system a deformable obturator element capable of being introduced in a deformed state inside a member through the orifice is used. In a position of use the obturator element has a substantially flat face that is applied in a tight manner on an inner face of the organ or vessel. The obturator element has a first portion of wire unwindable by pulling from its center. The system also uses an extractor element that consists of a second portion of wire extending from substantially the center of the obturator element. The extractor element is used to bring the flat face into contact with the inner face of the organ. After the orifice has been obturated the extractor element is used to remove the obturator element from the orifice.

15 Claims, 6 Drawing Sheets

SYSTEM FOR TEMPORARILY OBTURATING AN ORIFICE IN A PERFORATED ORGAN, SUCH AS A VESSEL

FIELD OF THE INVENTION

The present invention relates to a system for temporarily obturating an orifice in a perforated organ, such as in particular a vessel having undergone an operation.

The invention is applicable in the medical domain, principally in the treatment of disorders of the blood vessels, but may also be used for the treatment of other hollow organs such as the bladder, gall bladder or intestines.

BACKGROUND OF THE INVENTION

It is known that, for operations on the blood vessels, with percutaneous approach, it is necessary to prevent any hemorrhage when the apparatus introduced in the vessel is withdrawn.

A first, currently used solution to achieve this consists in applying a manual compression at the point of puncture. However, this solution is not entirely satisfactory, as it requires either the intervention of a specialist for a relatively long duration (30 minutes to 2 hours), or the use of a system of assisted compression which is cumbersome and generally poorly tolerated by the patient.

Another solution to avoid the risks of hemorrhage consists of introducing in the path of puncture a small pad made of a bio-resorbable matter such as, for example collagen. However, although this avoids the drawbacks of a manual compression, this solution requires the implantation of a foreign body whose possible migration in the vessel may prove extremely dangerous.

Under these conditions, it is an object of the present invention to solve the technical problem by providing a system for temporarily obturating an orifice in a perforated organ, which may be employed relatively easily, is safe for the patient, and which may easily be produced on an industrial scale.

SUMMARY OF THE INVENTION

The solution for solving this technical problem according to the present invention consists in a system for temporarily obturating an orifice in a perforated organ, such as in particular a vessel having undergone an operation, characterized in that it comprises:

- a deformable obturator element capable of being introduced in the deformed state inside said member through an orifice and constituted by a first portion of wire presented in position of the use in a substantially flat configuration, said first portion of wire being unwindable by rolling from its centre and comprising a tight face adapted to be applied on the inner face of said organ, in order to obturate said orifice; and
- an extractor element constituted by a second portion of wire, extending from the first wire substantially at its center and which, in position of use, passes through said orifice and extends outside said organ, thus forming a means making it possible, by pulling, to bring said tight face into contact with the inner face of the organ in order to obturate said orifice for a sufficient length of time to allow shrinkage thereof by natural reconstruction of the organ, then to extract said portion of wire by unwinding, when said orifice is sufficiently shrunk.

As will be readily understood, this novel system according to the invention effects a temporary, internal, mechanical obturation of the perforated organ, for a sufficient time to allow natural reconstitution thereof.

This system is extracted when the orifice resulting from the perforation is sufficiently narrowed, with the result that such extraction is effected without traumatizing the wall of the vessel.

According to a presently preferred embodiment of the invention, the first portion of the wire constituting the deformable obturator element mentioned above presents a flat spiral configuration.

According to another embodiment of the invention, it presents a knitted network configuration.

Said first portion of the wire advantageously comprises a face coated with a continuous film of polymer forming said tight face.

According to a particular characteristic, said obturator element is made by heating under pressure a wire coated with a thermoplastic polymer and formed in a spiral by winding on itself, or knitted.

The first and second portions of the wire may preferably be constituted by a single wire or by sections of wire joined together.

According to a particular feature, said first and second portions of the wire may preferably be constituted by a single micro-tube, or by sections of micro-tube connected together in tight manner; the part of the micro-tube constituting said first portion of the wire further comprising micro-holes in the wall constituting it. This conformation renders possible an intraparental injection through the first portion of the wire of a product capable of accelerating the phenomenon of healing.

According to a particular feature, the obturation system according to the invention comprises:

- a first sheath inside which is disposed a major part of the second portion of the wire constituting the extractor element;
- a pusher comprising a longitudinal housing traversing it, preferably centrally, and adapted to house said first sheath and whose end is shaped to enable the obturator element to be pushed;
- a second sheath inside which are disposed said pusher and said obturator element in the deformed state.

BRIEF DESCRIPTION OF THE DRAWINGS

The invention will be more readily understood on reading the following description given by way of non-limiting example, with reference to the accompanying drawings, in which:

FIGS. 1A to 1D illustrate a process for manufacturing an obturator element and the extractor element associated therewith, in a presently preferred embodiment of the invention, and more precisely:

DETAILED DESCRIPTION OF THE DRAWINGS

The perforated organ chosen by way of example in the following specification is a blood vessel 10 having undergone an operation, such as for example the introduction of a catheter for the treatment of a stenosis.

The expression "position of use" used in the present Description and Claims designates the position in which the orifice 2 of the vessel is obturated.

Referring now to the drawings, and firstly to FIGS. 1A to 1D, a process of manufacturing an obturator element and the extractor element associated therewith, in accordance with a presently preferred embodiment of the invention, will firstly be described.

Figure 1A:
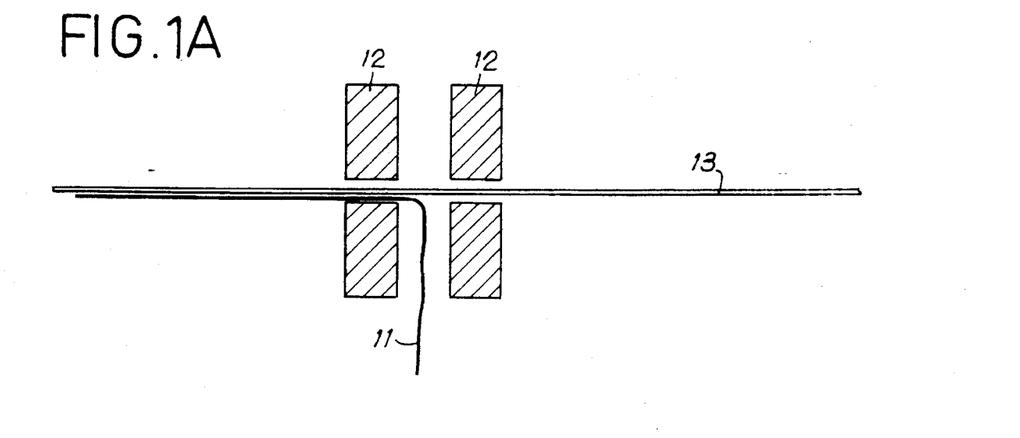
FIG. 1A illustrates the initial step of this process.
Figure 1B:
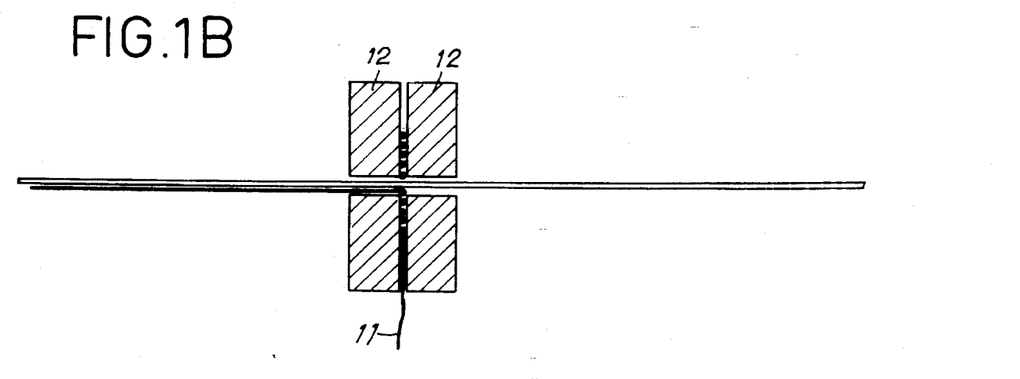
FIG. 1B illustrates the winding in a spiral of the first portion of the wire constituting the obturator element.
Figure 1C:
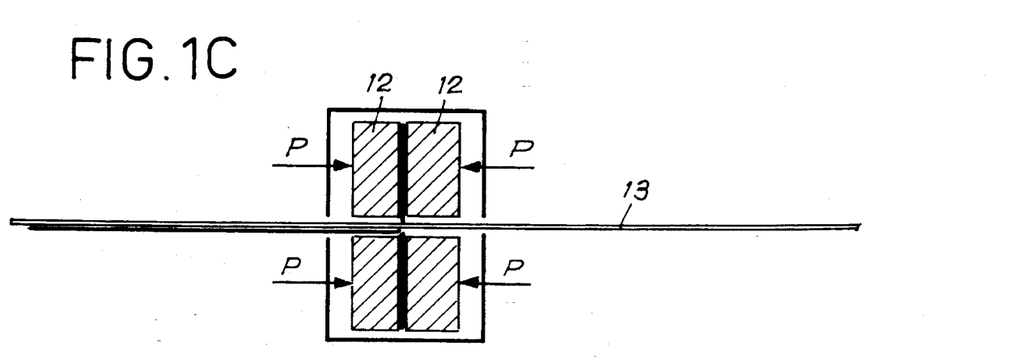
FIG. 1C illustrates the production of the tight face of the obturator element.
Figure 1D:
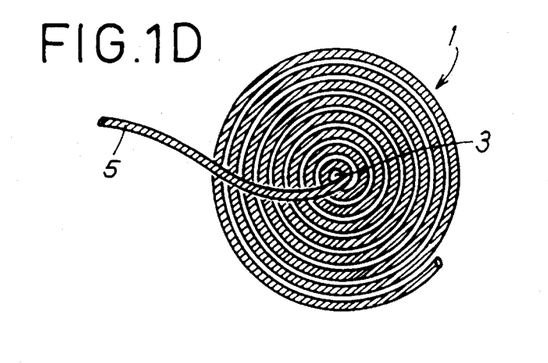
FIG. 1D represents the product tight face issuing from the process resulting from the steps represented in FIGS. 1A to 1C.

According to this embodiment, the obturator element presents substantially the shape of a flat washer constituted by a the wire or tube 11 wound on itself to constitute a spiral, whilst the extractor element 5 is constituted by a portion of the wire or tube extending from said spiral substantially at its center 3 (FIG. 1D).

In the example shown, the portions of the wire constituting the obturator element and the extractor element are constituted by a single wire. It is obvious that these elements may also be constituted by identical or different sections of the wire connected together by any appropriate means.

In addition, the portions of the wire constituting the obturator element and the extractor element may be constituted by a single micro-tube, or by sections of micro-tube connected together in tight manner; that part of micro-tube constituting the obturator element further comprising in its wall micro-holes for the injection of a product capable of accelerating healing.

The wire or tube 11 used will advantageously be constituted by a thermoplastic matter such as in particular a polyamide, and preferably a polyurethane such as for example the product marketed under the Trademark Pellethane. It may also be constituted by a metal armature coated with a thermoplastic material such as the one mentioned above.

To wind the wire 11 on itself, a mould may be used, constituted by two metal cylinders 12 each comprising a substantially central hole intended for the passage of a stainless steel rod 13.

In a first step shown in FIG. 1A, the wire 11 is passed through the hole in one of the cylinders 12 so that its free end is disposed between the two cylinders 12.

The two cylinders are then brought closer to each other and the wire 11 is wound on itself around the rod 13, between said cylinders, so as thus to constitute a spiral as shown in FIG. 1B.

In order to constitute a tight face 4 intended for obturating the orifice in the perforated organ, the assembly constituted by the mould and the wire spirally wound between the two cylinders, is disposed inside an enclosure.

A slight pressure P is then applied on the mould, then the temperature within the enclosure is taken to a sufficient value to effect heat-sealing of the wire on itself (FIG. 1C).

Such sealing must be sufficient to guarantee a perfect tightness of the obturator element in position of use whilst allowing an unwinding of the portion of the wire constituting the spiral without detachment of particles of matter in the organism.

The values of the pressure P to be applied on the mould, of the temperature within the enclosure and of the heating time may easily be determined by the man skilled in the art, in order to attain the object sought after.

In the example which has just been described, the obturator element presents a flat spiral configuration.

It may also be envisaged to produce this element by knitting a wire or tube of the same nature as indicated hereinabove, the network thus knitted having to be unwindable from its center.

A tight face may also be obtained in that case by heating the knitted piece under pressure.

The dimensions of the obturator element 1 must of course be greater than those of the orifice to be obturated.

The obturator element is intended to be introduced inside the perforated organ. It is therefore, necessary that its structure be deformable.

This possibility will generally be obtained by producing the obturator element in flat form, which makes it possible to deform it for example by winding, with the result that its dimensions in the deformed state may allow its introduction through the orifice in the perforated organ.

The obturator element 1 will generally be introduced inside the organ by means of an introducer or a pusher, as will be explained hereinbelow.

Figure 2A:
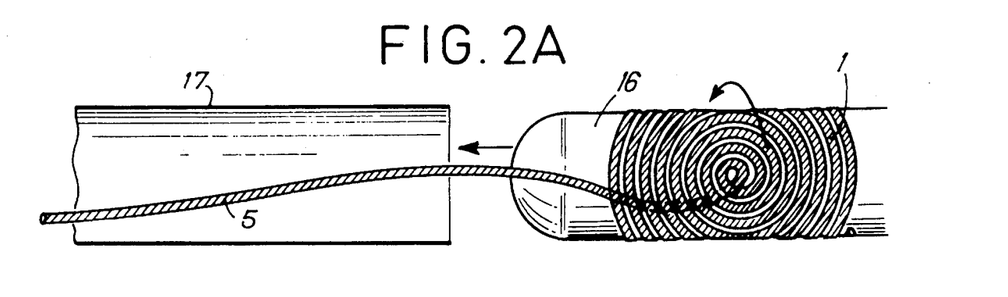
FIG. 2A is a view in longitudinal section illustrating the positioning of the obturator element in the deformed state inside a sheath.

In order to facilitate its introduction inside the introducer element, the obturator element will be wound around a metal matrix 16 with hemi-spherical head, and introduced in a sheath 17 whose outer dimensions are slightly smaller than the inner dimensions of the introducer element (cf. FIG. 2A).

It should be noted that the portion of the wire constituting the extractor element 5 traverses the sheath 17 as shown.

Figure 2B:
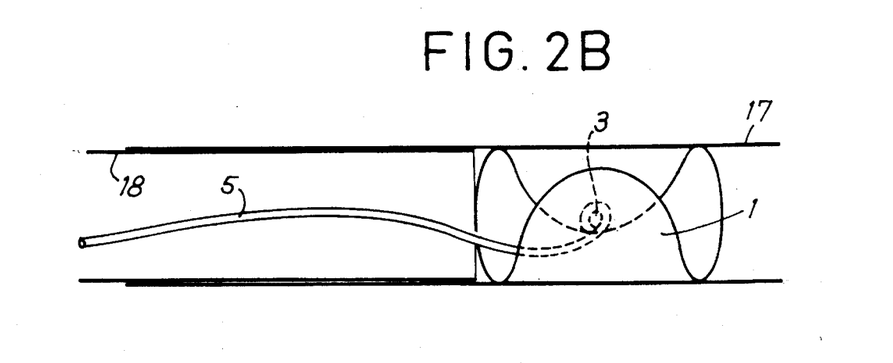
FIG. 2B is a view similar to FIG. 2A illustrating the obturator element inside the sheath.

After having withdrawn the cylindrical matrix 16, a pusher 18 is introduced at the free end of the sheath, the pusher capable of being traversed by the portion of the wire constituting the extractor element 5.

Referring now to FIGS. 3A to 3F, the use of the temporary obturation system according to the invention will now be described.

Figure 3A:
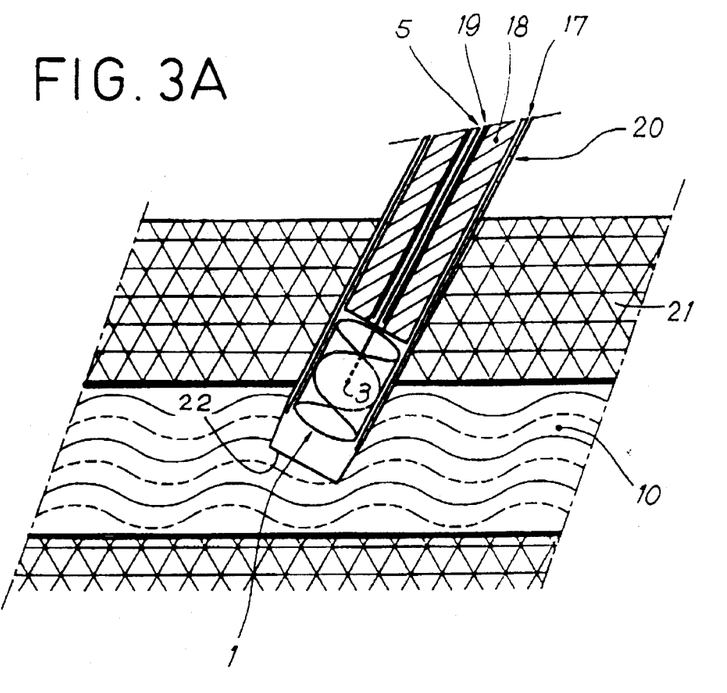
FIG. 3A is a view in longitudinal section illustrating the initial phase of introduction of an obturation system according to the present invention inside a vessel.

FIG. 3A is a view in longitudinal section illustrating the initial phase of introduction of this system inside a vessel 10.

Reference Number 21 represents the structure outside the organ, i.e. in the example chosen, the epidermis/dermis/fat/muscle assembly.

Reference Number 20 represents the introducer element inside which is disposed the sheath 17/pusher 18/obturator element 1/extractor element 5 assembly.

In the example shown, the portion of the wire constituting the extractor element 5 is itself introduced inside a sheath 19 in order to facilitate subsequent unwinding.

In addition, the pusher 18 comprises a longitudinal housing traversing it in substantially central manner, intended to receive this sheath 19.

Figure 3B:
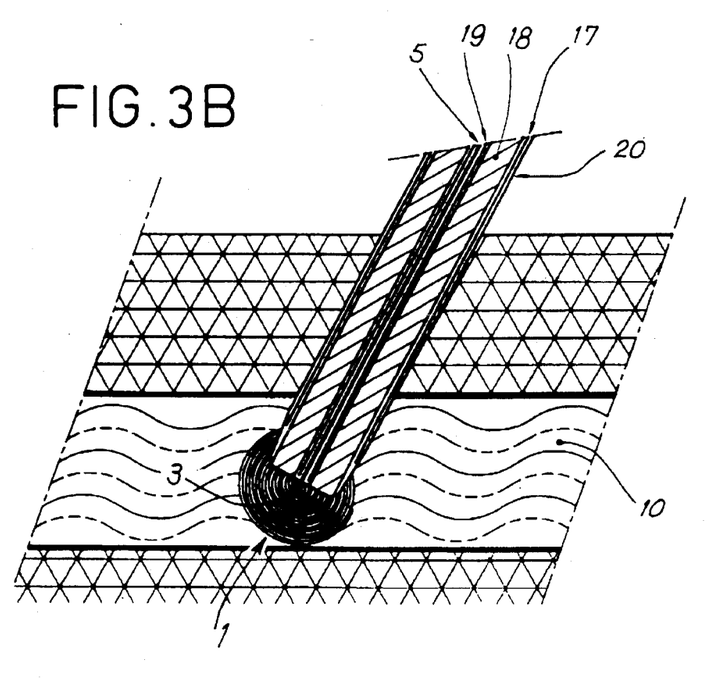
FIG. 3B is a view similar to FIG. 3A illustrating the operation of releasing the obturator element inside the vessel.

When the end 22 of the introducer 20 is located inside the vessel 10, the obturator element 1 is then released by displacing the pusher 18 towards the free front end 22 of the introducer element 20 (FIG. 3B).

The obturator element 1 then resumes its initial substantially flat shape.

Figure 3C:
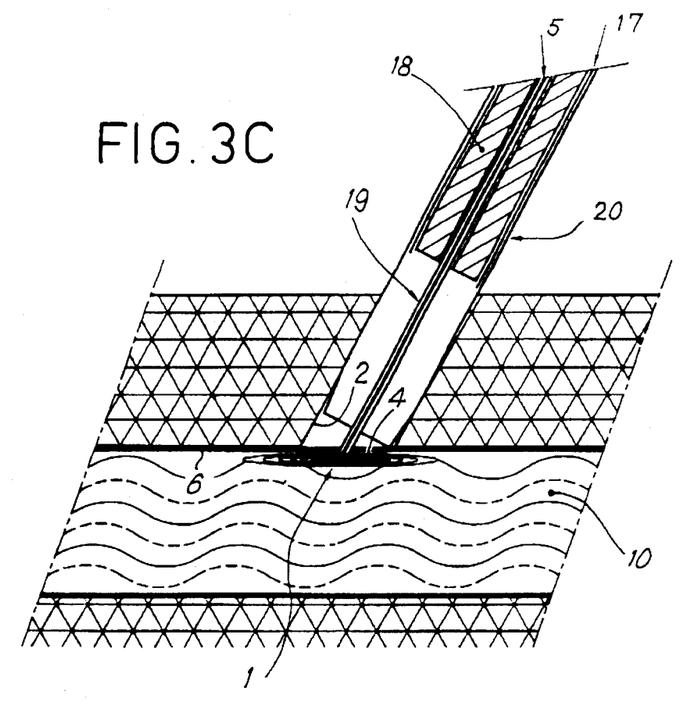
FIG. 3C is a view similar to the preceding ones, illustrating the positioning of the obturator element in contact with the inner face of the organ in order to obturate an orifice.

The introducer element 20, the sheath 17 and the pusher 18 are then withdrawn and the tight face 4 of the obturator element 1 is placed in contact with the inner face 6 of the organ in order to obturate the orifice 2, by pulling of the portion of the wire constituting the extractor element 5 (cf. FIG. 3C).

The front end of the sheath 19 inside which lies the portion of the wire defining the extractor element 5 is disposed at the level of the contact surface between the tight face 5 and the inner face 6.

Figure 3D:
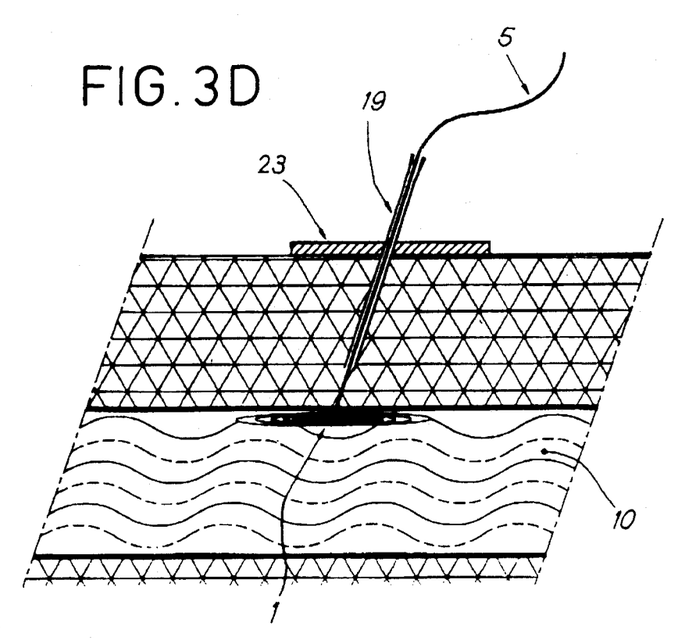
FIG. 3D is a view similar to the preceding ones illustrating the maintenance of the obturator element in position of use.

In order to maintain the obturator element 1 in position of obturation of the orifice, it may be advantageous to immobilize the sheath 19 with the aid of a holding element such as a clip 23, after having withdrawn from the orifice 2 the assembly constituted by the introducer 20, the sheath 17 and the pusher 18 (cf. FIG. 3D).

The obturator element 1 is maintained in this position for a sufficient length of time to allow the orifice 2 to shrink by natural reconstruction of the perforated organ.

Figure 3E:
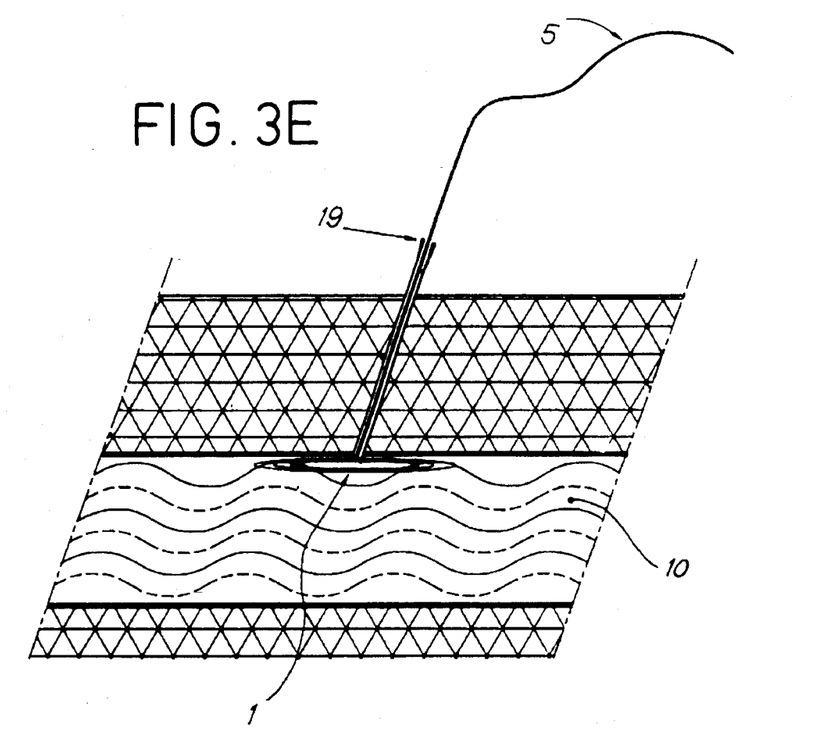
FIG. 3E is a view similar to the preceding ones illustrating the initial phase of unwinding the first portion of the wire constituting the obturator element.
Figure 3F:
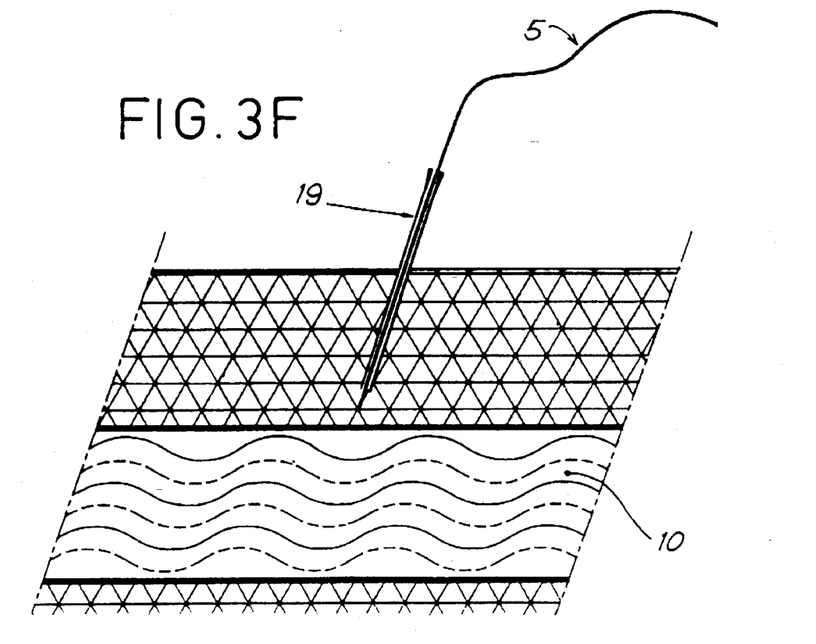
FIG. 3F is a view similar to the preceding ones illustrating the final phase of unwinding of the first portion of the wire constituting the obturator element.

When the orifice is sufficiently shrunk, the clip 23 is loosened and, holding the clip 23/sheath 19 assembly, the portion of the wire constituting the extractor element 5 is drawn so as thus to unwind the portion of the wire constituting the obturator element 1 (FIG. 3E). Finally, an orifice is obtained whose dimensions are those of the sheath 19, i.e. sufficiently small dimensions to avoid any risk of hemorrhage, the organ being virtually completely healed.

Figure 4:
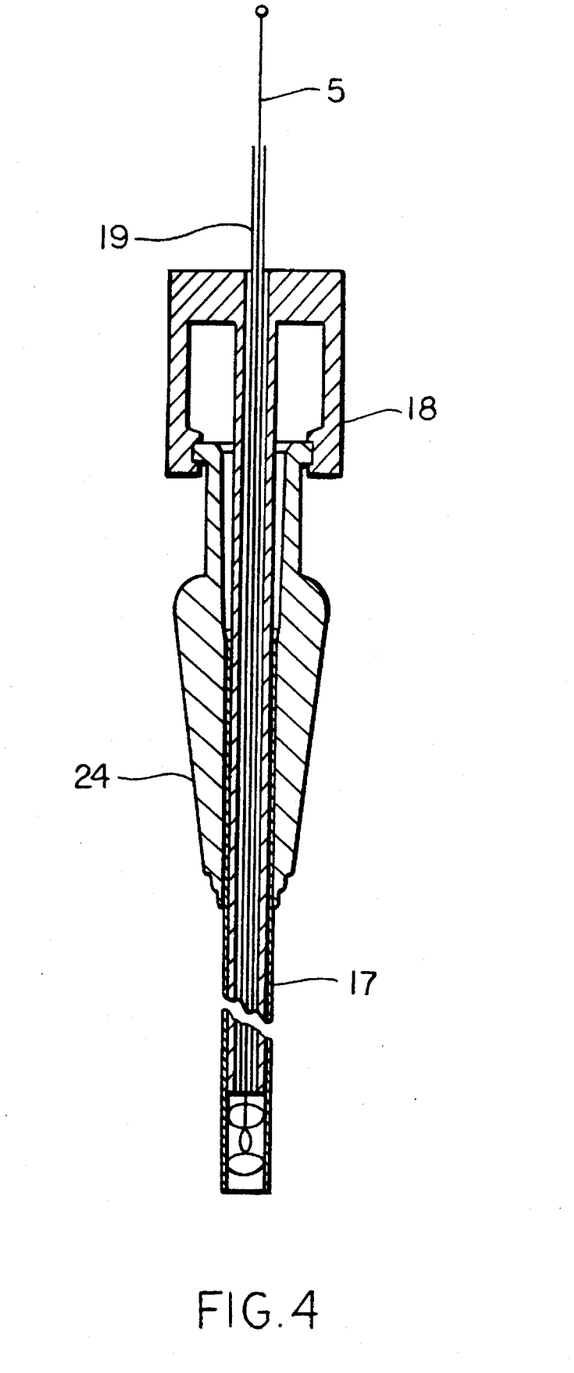
FIG. 4 is a view in longitudinal section of a complete temporary obturation system according to the invention.

FIG. 4 shows in longitudinal section a temporary obturation system according to the present invention.

As may be seen, this system further comprises a base 24 constituted by a ring capable of being clipped on the head of the pusher 18 shaped to that end.

This base is intended to make it possible to fix the introduction system on an introducer by an effect of clipping.

The obturation system which has just been described is relatively easy to use, under good conditions of safety for the patient and may be produced relatively easily on an industrial scale.

What is claimed is:

1. A system for obturating an orifice in an organ or vessel comprising:

a deformable obturator wire element having a central portion, in position of use, a substantially flat face adapted to be applied in a tight manner on an inner face of said organ or vessel in order to obturate said orifice, a means for introducing said deformable obturator element through said orifice;

said obturator element consisting of a first portion of said wire which is spirally wound to said center so as to be unwindable by pulling from its center;

an extractor element consisting of a second portion of wire extending from substantially the center of the obturator element;

said extractor element, in position of use, passing through said orifice and extending outside said orifice, using said extractor element to bring said substantially flat face into contact with the inner face of the organ, and after the orifice has been obturated for a time sufficient to allow for shrinkage of the orifice, using said extractor element to remove said obturator element from the orifice by unwinding said first portion of wire.

2. The obturation system of claim 1 wherein said first portion of the wire presents a flat spiral configuration.

3. The obturation system of claim 1 wherein said first portion of the wire presents a knitted network configuration.

4. The obturation system of claim 1, wherein said obturator element is made by heating under pressure a wire coated with a thermoplastic polymer and formed in a spiral by winding on itself.

5. The obturation system of claim 4, wherein said thermoplastic polymer is a polyurethane.

6. The obturation system of claim 4, wherein said obturator element is made by heating a wire coated with a thermoplastic polymer and knitting said wire to form a spiral.

7. The obturation system of claim 6, wherein said thermoplastic polymer is a polyurethane.

8. The obturation system of claim 4, wherein said thermoplastic polymer is a polyurethane.

9. The obturation system of claim 1, wherein said first and second portions of wire are constituted by a single wire.

10. The obturation system of claim 1 wherein said first and second portions of the wire is constituted by a single micro-tube; the micro-tube constituting said first portion having a wall and micro-holes in the wall.

11. The obturation system of claim 1, further comprising—a first sheath inside which is disposed a significant part of the second portion of the wire constituting the extractor element;

a pusher comprising a longitudinal housing adapted to house said first sheath and whose end is shaped to enable the obturator element to be pushed; and a second sheath inside which are disposed said pusher and said obturator element in the deformed state.

12. The obturation system of claim 11, wherein it further comprises an element for maintaining the first sheath in position.

13. The obturation system of claim 12 wherein the element for maintaining the first sheath in position is a clip.

14. The obturation system of claim 1 wherein said first and second portions of the wire is constituted by sections of micro-tube connected together in a tight manner, the micro-tube constituting said first portion having a wall and micro-holes in the wall.

15. A method of obturating an orifice in an organ or vessel comprising introducing a spirally wound deformable obturator element through said orifice by using a pusher;

said obturator element comprising a wire having a center portion; said wire in a substantially flat configuration forming a tight face adapted to be applied on an inner surface of said orifice, and a first portion of said wire being unwindable by pulling from its center; an extractor element extending substantially from the center of the obturator element, said extractor element extending through said orifice to the outside said orifice, using said extractor element to bring said tight face into contact with the inner surface of the orifice, and after the orifice has obturated for a time sufficient to allow for shrinkage of the orifice by natural reconstruction of said organ or vessel, using said extractor element to remove said tight face from the orifice by unwinding said tight face.

* * * * *